United States Patent [19]

Zimmermann et al.

[11] 4,453,320

[45] Jun. 12, 1984

[54] PROCESS FOR CHANGING THE WATER CONTENT OF WATER-ABSORBING OR WATER-RELEASING MATERIAL

[75] Inventors: Wolfgang Zimmermann; Albrecht Harréus, both of Kelkheim; Richard Gutte, Frankfurt am Main, all of Fed. Rep. of Germany

[73] Assignee: Hoechst Aktiengesellschaft, Frankfurt am Main, Fed. Rep. of Germany

[21] Appl. No.: 312,271

[22] Filed: Oct. 16, 1981

[30] Foreign Application Priority Data

Oct. 18, 1980 [DE] Fed. Rep. of Germany ....... 3039386

[51] Int. Cl.³ ............................................... F26B 5/00
[52] U.S. Cl. ......................................... 34/95; 210/767; 252/194; 426/410; 428/451; 428/522
[58] Field of Search .................. 34/89.1, 95; 252/194; 210/767, 774; 428/522, 451; 426/106, 127, 410, 419

[56] References Cited

U.S. PATENT DOCUMENTS 3,523,568 8/1970 van Leeuwen .
4,082,854 4/1978 Yamada et al. ...................... 426/127
4,191,805 3/1980 Nolte .
4,323,492 4/1982 Zimmermann et al. .

FOREIGN PATENT DOCUMENTS 19549 3/1973 Japan .

*Primary Examiner*—Larry I. Schwartz
*Attorney, Agent, or Firm*—Curtis, Morris & Safford

[57] ABSTRACT

The water content of a material, which tends to either absorb water or to release water, is changed with the aid of a film, which at least partially separates the material from the adjacent space and is impermeable to liquid water but permeable to gaseous water. Polyvinyl alcohol with a particular degree of polymerization and degree of hydrolysis is used as the film material. The film can be mechanically or chemically after-treated. The moistening or de-moistening of the material, which is solid, liquid or gaseous, is effected, utilizing a water vapor pressure gradient, under very mild conditions.

10 Claims, No Drawings

PROCESS FOR CHANGING THE WATER CONTENT OF WATER-ABSORBING OR WATER-RELEASING MATERIAL

The invention relates to a process for changing the water content of water-absorbing or water-releasing material with the aid of a film at least partially separates this material from the adjacent space and is impermeable to liquid water, but permeable to gaseous water.

It is known that polyvinyl alcohol (PVAL) has good water solubility, and that this property is dependent on the ester number and can be varied by chemical after-treatment, for example by partial acetalisation. The thermoplastic deformability of PVAL, which is processed, for example by pressing or extruding, to give films which are soluble in cold water, is likewise known; such films are used, for example, for packing dyes, poisons, pesticides and washing agents (see Kunststoff-Handbuch (Plastics Handbook), volume 11 (1971), pages 509 to 516). The water solubility of films of this type can be affected by mechanical treatment, for example stretching, or by chemical after-treatment, for example acetalisation.

The object of the invention is the moistening or de-moistening of solids, liquids or gases using a film of PVAL which serves as a release film between the material which is to be moistened or de-moistened and its environment.

The invention relates to a process for changing the water content of water-absorbing or water-releasing material with the aid of a film which at least partially separates this material from the adjacent space and is impermeable to liquid water, but permeable to gaseous water, which comprises using as the film a film made of polyvinyl alcohol which is water-insoluble at a temperature below 80° C., which has an ester number of from 0 to 200 mg of KOH/g and the 4 percent strength by weight aqueous solution of which exhibits a viscosity of 4 to 100 mPa.s at a temperature of 20° C., the film being mechanically or chemically after-treated, as appropriate, and carrying out the change of the water content on a solid, a liquid or a gas.

The process according to the invention is used for changing the water content of water-absorbing or water-releasing material using a film which completely or partially separates this material from the adjacent space and, under normal conditions, is impermeable to liquid water, but permeable to gaseous water. This process is suitable for drying or moistening any desired material, which can be solid, liquid or gaseous. In this process, the essential characteristic of the invention is the use of a PVAL film for all areas of use which are concerned with the moistening and de-moistening of particular materials, the evaporation of the water being effected with the utilization of a water vapor pressure gradient. The process according to the invention is, in particular, a method for drying water-containing material under very mild conditions, that is to say, without using elevated temperatures.

The film used according to the invention is prepared from a polyvinyl alcohol which has an ester number of from 0 to 200 mg of KOH/g, preferably 10 to 150 mg of KOH/g, and the 4 percent strength by weight aqueous solution of which exhibits a viscosity of 4 to 100 mPa.s, preferably 10 to 60 mPa.s, at a temperature of 20° C. The film is insoluble in water at a temperature below 80° C., particularly below 60° C. and preferably in the range of from 0 to 50° C.

The water solubility of the film can be controlled mechanically, preferably by biaxial stretching, or chemically, preferably by partial crosslinking. Compounds which react with the hydroxyl groups of PVAL are used as crosslinking agents in this process. Bifunctional compounds, such as bis-epoxides and diisocyanates, and, in particular, formaldehyde or compounds which split off formaldehyde, and dialdehydes, for example glyoxal or terephthalic aldehyde, are particularly suitable.

Thermoplastically workable, plasticizer-containing, free-flowing, non-adhesive PVAL granules are particularly suitable as a starting material for the preparation of the film; these consist to at least 70 percent by weight, preferably at least 90 percent by weight, of particles having a diameter of from 0.8 to 4 mm, in which a plasticizer and, if appropriate, a water-soluble or water-dispersable, high-molecular organic compound composed of fine particles are homogeneously distributed. These granules are prepared in a known manner by intensively and homogeneously mixing together 100 parts by weight of dry PVAL granules, which consist, to at least 70 percent by weight, of particles having a diameter of from 0.4 to 4 mm, with 5 to 50 parts by weight of a plasticizer—if appropriate in the presence of 1 to 15 parts by weight of a watersoluble or water-dispersable, high-molecular organic compound which is composed of fine particles and which consists of particles having diameters of at most 300 μm—in the presence of a quantity of water which is insufficient for dissolving the PVAL under normal conditions; during the mixing process, the temperature of the mixture is raised and again lowered in such a manner that the PVAL particles swell and temporarily agglomerate (see European Published Application No. 4587).

The film used according to the invention is prepared by customary processes, particularly by the casting process, the slot-die (fishtail die) extrusion process or, preferably, the extrusion blowing process. The thickness of the film is customarily in the range of from 10 to 200 μm, preferably 30 to 100 μm.

Provided that a water vapor pressure gradient is present, any desired material which can be completely or partly surrounded with the PVAL film or completely or partially separated by the film from the space adjacent to the material can be moistened or de-moistened by the process according to the invention.

For the purposes of drying, it is advisable to store the material in a closed container, for example a bag or tube, composed of the PVAL film. However, it is also often sufficient merely to cover the material superficially with the film, the lateral admission of air not affecting the drying process adversely. Such a drying process can be carried out in the open air, and an external wetting of the film by dew or rain has no effect on the drying of the material covered with the film.

Vegetable material, for example drugs (leaves, blossom, fruit and roots), luxury consumables (coffee, tea, tobacco), as well as herbs, timber and grass, is particularly suitable for drying by the process according to the invention. Foodstuffs based on vegetable or animal materials and medicaments having vegetable or chemical active ingredients can also be dried under mild conditions in the same manner. In this process, ay aromas contained in the material are largely retained by means of the film. Building materials, such as mortar, gypsum and cement, can also be dried and protected from rain and sprayed water by covering with a PVAL film.

Furthermore, the process according to the invention affords the possibility of concentrating aqueous solutions or dispersions of inorganic or organic substances by the withdrawal of water. In this process, it is advantageous to use the PVAL film in the form of a tube through which the solution or dispersion is conducted. This method can be used in the same manner for water-in-oil emulsions and oil-in-water emulsions. Water-containing solvents, for example methanol, ethanol or acetone, are preferably dehydrated by being stored for some time in a bag which is composed of PVAL film and is closed by welding, in an atmosphere with a low relative humidity.

A further method of drying with the aid of the PVAL film comprises bringing a drying agent, for example silica gel, which is enclosed in a bag of the PVAL film by welding, into contact with the goods to be dried, which are contained in a closed vessel. In this manner, both solid substances and objects as well as liquids and gases can be dried. In particular, hygroscopic substances and moisture-sensitive goods can be dried and kept dry with the aid of the process according to the invention. The same applies for industrially used objects and apparatuses, for example scales, electrical or optical instruments and electronic components, which are water-sensitive.

The process according to the invention can be preferably used on objects in the sanitation field or hygiene field. For example, the PVAL film can be connected with a porous layer of fiber material, for example of fiber fleece and/or wadding, whereby laminates are obtained which are impermeable to liquid water but permeable to water vapor, and which are suitable for the preparation of bandages, diapers and undersheets for hospital beds.

Furthermore, the film used according to the invention can be employed in the form of a multi-layer laminate, which contains the film as the middle layer, particularly in the synthetic leather sector for the preparation of laminates which are permeable to water vapor but impermeable to liquid water, particularly as the intermediate layer between perforated soft PVC plates.

Changing the water content of the air of rooms which are used by people, particularly dwelling rooms and work rooms, is a particular variant of the process according to the invention. In this process, changing the water content comprises a moistening or de-moistening of the room, depending on the requirements of the particular case. For specifically moistening a room, the PVAL film is advantageously used in the form of a tube system; in this system, the water contained in the tube slowly vaporizes through the tube wall. this method of moistening rooms has the advantage that the water-hardening substances contained in the tap water are not deposited on the internal wall of the tube, but collect at the bottom and can be removed in a simple manner by flushing the tube with fresh water.

The examples which follow show some uses of the process according to the invention. Percent data are relative to weight, in each case.

EXAMPLE 1

A film having a thickness of 30 μm is prepared from commercial polyvinyl alcohol granules, which contain 20% of glycerol as a plasticizer, by extrusion blowing. The PVAL has an ester number of 20 mg of KOH/g, is insoluble in water up to a temperature of 50° C., and the 4 percent strength aqueous solution of PVAL has a viscosity of 20 mPa.s.

3 identical bowls with a diameter of 7 cm and a height of 3 cm are each filled with the same quantity of water. 2 of these bowls are hermetically closed with the PVAL film described above; the third bowl is used for a blank test. The three bowls are then placed in a climatically controlled room (23° C., 50% relative atmospheric humidity), one of the bowls which are closed with the film being placed upside down on a grid, so that the total surface of the film is in contact with the water. In the blank test, the water has evaporated after 7 days. The water in the bowl standing upside down has evaporated after 8 days, and the water in the bowl covered normally with the film has evaporated after 10 days.

EXAMPLE 2

(a) Fresh tobacco leaves are individually enclosed by welding in a film of the type described in Example 1, and are hung in a climatically controlled room (23° C., 50% relative atmospheric humidity). After 10 days, the weight of the tobacco leaves is still 66%, on average, of the starting value.

(b) Fresh tobacco leaves are individually placed in bags prepared from the film described in Example 1, and the bags are hung in the open air with the opening pointing downwards. After 10 days, the weight of the tobacco leaves is 50%, on average, of the starting value.

EXAMPLE 3

(a) A pile of freshly mown grass having a water content of 80% is covered with a film of the type described in EXAMPLE 1, and is left for 4 weeks. The water content of the grass is thereafter only 30%.

(b) Freshly mown grass having a water content of 80% is enclosed by welding in a sack composed of a film of the type described in Example 1. After storage for 4 weeks, the grass has a water content of 25%.

EXAMPLE 4

50 g of caustic soda tablets are introduced into a test tube, and a bag which is made of a film of the type described in Example 1 and which is filled with dried silica gel is placed on these tablets. The test tube is then closed with a cotton wool plug and is placed in a climatically controlled room (23° C., 50% relative atmospheric humidity). After 5 weeks, the tablets are still completely dry and free-flowing.

EXAMPLE 5

A mixture of 90% of acetone and 10% of water is introduced into a bag made of a film of the type described in Example 1; the bag is closed so that it is airtight and is hung in a climatically controlled room (23° C., 50% relative atmospheric humidity). After a period of storage of 3 weeks, the water content of the mixture is only 3%.

EXAMPLE 6

A 10% strength cane sugar solution is introduced into a bag made of a film of the type described in Example 1; the bag is closed by welding and is hung in a climatically controlled room (23° C., 50% relative atmospheric humidity). After a period of storage of 1 week, the solution is syrupy, and after a further 3 days, the sugar begins to crystallize in the bag.

EXAMPLE 7

Firstly a layer of cellulose wadding and then a layer of polyester fiber fleece are applied on a film of the type described in Example 1. The resulting laminate is used as a hospital bed under-sheet, which is very absorptive and gradually releases absorbed moisture downwards, in the form of water vapor.

EXAMPLE 8

A tube, which has a total length of 5 m and a diameter of 2 cm and forms a closed system, is attached to a wooden frame in a dwelling room. The tube consists of a film of the type described in Example 1. Water is fed continuously and slowly through the tube, with the aid of a pump. A fan, which blows air through the system into the room, is situated behind the tube system. The evaporated water is replaced from time to time. The moistening of the room is carried out uninterruptedly for several months, without encrustations forming on the tube walls.

EXAMPLE 9

A film of the type described in Example 1 is bonded on both sides with a 1 mm thick plate of perforated soft PVC, by pressing at a temperature of 150° C. The resulting laminate is impermeable to liquid water but permeable to water vapor, and is used for the manufacture of articles of synthetic leather.

EXAMPLE 10

Two pieces of fibrous leather substitute of a size corresponding to the German industrial standard DIN A 6 and of 0.5 mm thickness each are bonded unilaterally with a commercial dispersion containing a copolymer of vinyl acetate and ethylene, in a quantity of 100 g/m$^2$. A film of the type described in Example 1 is inserted between the bonded faces of said pieces. The resulting structure is pressed for 10 minutes in a hydraulic press under a pressure of 20 bars to give a laminate.

The steam permeability of the laminate of fibrous leather substitute is examined in the manner descirbed in Example 1. To this end, the laminate is placed on the bowl containing 10 g of water and glued on the rim thereof.

The total amount of water has evaporated from the bowl covered with the laminate after 11 days.

We claim:

1. A process for changing the water content of water-absorbing or water-releasing material comprising,
    at least partially separating the material from an adjacent space with the aid of a film which is impermeable to liquid water, but permeable to gaseous water,
    said film being made of polyvinyl alcohol which is water-insoluble at a temperature below 80° C., which has an ester number of between 0 and 200 mg of KOH/g and the 4 percent strength of weight aqueous solution of which exhibits a viscosity of 4 to 100 mPa.s at a temperature of 20° C., the film being mechanically or chemically after-treated, as appropriate, and
    placing said film between said material and an adjacent space to allow gaseous water to pass therethrough while preventing the passage of liquid water,
    said water absorbing or water releasing material being a solid, a liquid or a gas.

2. A process as claimed in claim 1, wherein the change of the water content is carried out for vegetable material.

3. A process as claimed in claim 1, wherein the change of the water content is carried out for a foodstuff.

4. A process as claimed in claim 1, wherein the change of the water content is carried out for a building material.

5. A process as claimed in claim 1, wherein the change of the water content is carried out for a hygroscopic substance.

6. A process as claimed in claim 1, wherein the change of the water content is carried out for an aqueous solution or dispersion.

7. A process as claimed in claim 1, wherein the change of the water content is carried out for an industrially used object.

8. A process as claimed in claim 1, wherein the change of the water content is carried out for the air of a dwelling room or work room.

9. A process as claimed in claim 1, wherein the film is used in connection with a porous layer of fiber material.

10. A process as claimed in claim 9, wherein the film is used in the form of a multi-layer laminate which contains the film as the middle layer.

* * * * *